United States Patent [19]

Handel et al.

[11] Patent Number: 5,047,527

[45] Date of Patent: Sep. 10, 1991

[54] PROCESS FOR THE PREPARATION OF MONOFUNCTIONALIZED CYCLIC TETRAMINES

[75] Inventors: Henri Handel, Brest; Jean-Jacques Yaouanc, Locmaria-Plouzane; Ayoub F. Zegzouti, Brest; Denis Malouala, Brest; Hervé des Abbayes, Brest; Jean-Claude Clement, Coat-Meal; Héléne Bernard, Plouguerneau; Guénaëlle Le Gall, Fouesnant, all of France

[73] Assignee: Centre National de la Recherche Scientifique (CNRS), Paris, France

[21] Appl. No.: 495,045

[22] Filed: Mar. 19, 1990

[30] Foreign Application Priority Data

Mar. 20, 1989 [FR] France ............................. 89 03600

[51] Int. Cl.$^5$ ........................................... C07D 257/02
[52] U.S. Cl. .................................................... 540/474
[58] Field of Search ........................................ 540/474

[56] References Cited

FOREIGN PATENT DOCUMENTS 0287436 10/1988 France ................................. 540/474

OTHER PUBLICATIONS

Chemical Abstract No. 85658a, vol. 96, No. 11, (Mar. 1982), p. 600.
Bouvier et al., Synth. React. Inorg. Met.-Org. Chem., "Synthesis and Characterization of Cyclamphosphate Sulfide and Selenide", vol. 17, No. 3, (1987), pp. 301–306.
Atkins et al., Tetrahedron Letters, "Polyaminophosphoranes III. P(III)-P(V) Tautomerism in Four Nitrogen Cage Phosphoranes", No. 52, (1978), pp. 5149–5152.
Dupart et al., Journal of the American Chemical Society, "Coordination Chemistry of Cyclamphosphorane, Access to Transition–Metal Cyclamphosphoranides, Crystal and Molecular Structure of CpMo(CO)2(Cyclamphosphoranide)", vol. 108, No. 6 (Mar. 1986), pp. 1167–1173.
Chemical Abstract No. 69559j, vol. 107, No. 8, (1987).
French Search Report, Application No. FR 8903600.

*Primary Examiner*—Robert T. Bond
*Attorney, Agent, or Firm*—Cushman, Darby & Cushman

[57] ABSTRACT

Process for the preparation of monofunctionalized cyclic tertramines of formula I

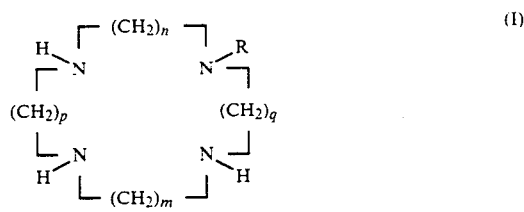

in which R denotes a saturated or unsaturated, especially polymerizable, organic radical, characterized in that the corresponding tetraazacycloalkane compound (according to formula II) is prepared, in which three of the four nitrogen atoms are bonded via covalent bonds with a single atom or group of intracyclic atoms A, in that this triprotected compound is reacted with an organic compound RX (of formula III), X denoting a nucleophobic group, and in that the tetraazacycloalkane compound which is tri-protected and monofunctionalized on the unprotected nitrogen (according to formula IV) thus obtained is deprotected.

12 Claims, No Drawings

PROCESS FOR THE PREPARATION OF MONOFUNCTIONALIZED CYCLIC TETRAMINES

The present invention, made at the Molecular Chemistry, Electrochemistry and Photochemistry Laboratory of the University of Western Brittany, a laboratory affiliated to the National Center for Scientific Research, relates to a process for the preparation of monofunctionalized cyclic tetramines.

Tetraazamacrorings are macrocyclic ligands which exhibit the characteristic of forming extremely stable complexes with ions of transition metals (from the manganese column to that of zinc, but also with lead, and the like). On the other hand, these molecules do not, or very barely, associate with alkali and alkaline-earth metals (see Host Guest Complex Chemistry I, II, III. F. Vogtle and E. Weber Edit., Springer Verlag, 1980, 1981 and 1984, and Coordination Chemistry of Macrocyclic Compounds, A. Melson Edit., Plenum, 1979).

Many applications are described in the literature in fields as diverse as electrochemistry (modified electrodes), catalysis, stabilization of unstable oxidation states or, furthermore, nuclear medicine. Each of these applications requires a specific modification of the tetranitrogenous ligand and therefore a recommencement of its synthesis.

Equally, the very high affinity of cyclic tetramines for metals which may be rare or precious metals (Cu, Ag, Au, Pd, Ru, Rh, Os, and the like) or, on the contrary, polluting metals (Zn, Cd, Hg, Pb, and the like) is also a potential source of advantageous applications. However, in this case too, in order to have the benefit of the properties of these molecules, a specific modification of their structure must be carried out for each of the envisaged applications. Thus, if it is desired to employ a cyclic tetramine to extract an ion from an aqueous phase towards an organic phase, a lipophilic group which will increase the solubility of the complex in organic solvents must be added to it. Similarly, to make a chelating ion exchange resin, the macroring must be attached to a polymer.

EP-A-0,287,436 illustrates the state of the art considered to be that most closely related. The monofunctionalization process described in this prior patent has made it possible to prepare known derivatives of cyclam as well as other new derivatives, both of cyclam and of other tetraazacycloalkanes, symmetrical or otherwise.

The objective of the present invention is precisely to develop a new method of monofunctionalization of this type of tetraazamacrorings, which can be applied in less constraining and more economical conditions, and which can therefore be exploited better on an industrial scale.

The new process which is the subject of the present invention is based on the blocking of three of the four nitrogen atoms of the ring by engagement in covalent bonds with a single intracyclic atom or group of atoms.

More precisely, the invention is aimed at a process for the preparation of monofunctionalized tetramines of formula I

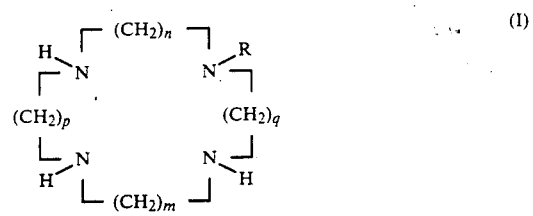

in which:
m=n=p=q=2, or
m=n=2 ; p=q=3, or
m=2 ; n=p=q=3, or
n=2 ; m=p=q=3, or
m=n=p=q=3, or
m=n=3 ; p=q=4, and R denotes a saturated or unsaturated, especially polymerizable, organic radical, characterized in that a triprotected tetraazacycloalkane compound is prepared, of formula II

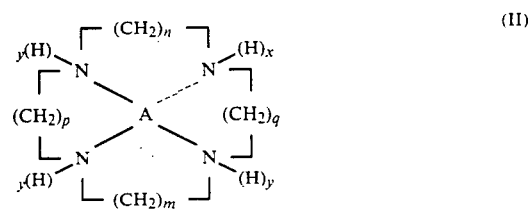

in which:
x and y denote, independently of each other, 1 or 0,
at least three of the four nitrogen atoms are bonded, via covalent bonds, with a single intracyclic atom or group of atoms A, and
the broken line denotes a covalent bond which may be formed between the fourth nitrogen atom and A; in that the triprotected tetraazacycloalkane compound of formula II is reacted with an organic compound of formula III $$R-X \qquad (III)$$

in which:
R has the meaning given in connection with formula I, and
X denotes a nucleophobic group, especially a halogen or a tosylate radical, to obtain a triprotected and monofunctionalized tetraazacycloalkane compound of formula IV

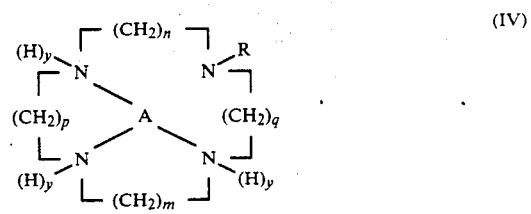

and in that the compound of formula IV is deprotected to obtain the corresponding compound of formula I.

In the above formulae II and IV the symbol A may, in particular, denote a boron atom or a metal-carbonyl group $M(CO)_3$ with M chosen from Cr, Mo and W, or else a P(O) or P(+) group. In the case where A denotes a P(+) group, the broken line of formula II then denotes a covalent bond formed between P(+) and the fourth nitrogen atom.

The first variant of the process according to the invention will be illustrated below with the aid of a reaction scheme relating to the monoalkylation of cyclam.

VARIANT A

The method employed for effecting the monoalkylation of tetraazamacrorings in an unambiguous manner turns to good account the property of metal carbonyls of the 6th group of forming nitrogenous complexes by reaction with amines, by substitution of one, then two, then three C=O ligands.

This process of monoalkylation according to the invention is highly selective. The monoalkylated compound alone is obtained. This process does not, therefore, require any additional purification stage. Furthermore, the protection and deprotection stages are quantitative and stoichiometric.

REACTION SCHEME a) Protection

The reaction of a tetraazamacroring with a metal carbonyl of the 6th group allows three of the four nitrogen atoms to be blocked:

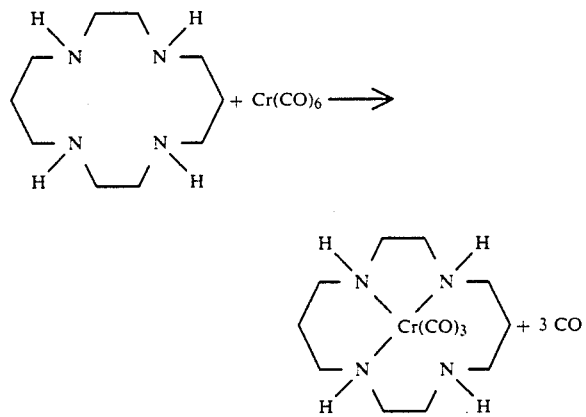

b) Alkylation

The reaction of alkylation with alkyl halides on the 4th nitrogen atom which is left free takes place in conventional SN$_2$ condition, with good yields.

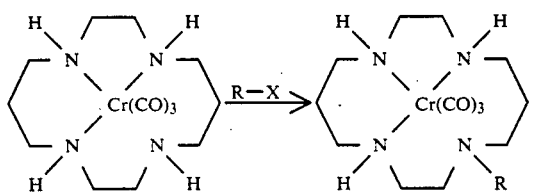

c) Deprotection

The removal of the Cr(CO)$_3$ protecting group is effected simply by air oxidation at acidic pH.

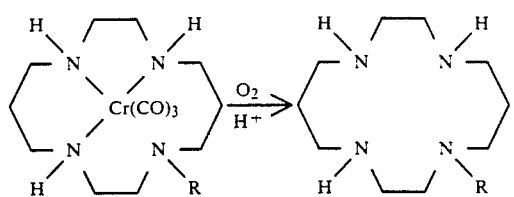

The second variant of the process according to the invention is also illustrated below with the aid of a reaction scheme relating to the monoalkylation of cyclam.

VARIANT B

This variant is also based on the intracyclic blocking of three of the four nitrogen atoms of cyclam. The triprotected intermediate of formula II is the phosphorotriamide which can be obtained, for example, according to the scheme below, as described by J.E. Richman and J.J. Kubale, J. Am. Chem. Soc. 1983, 105, 749:

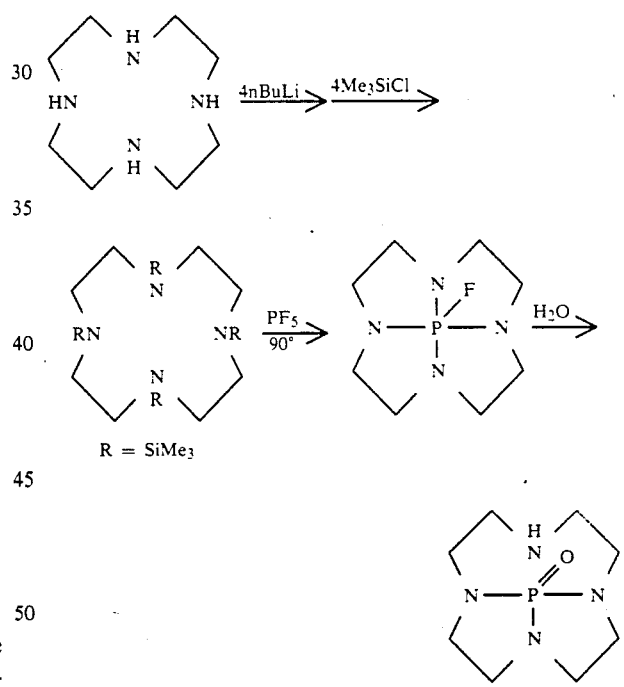

Similarly, the intermediate phosphorotriamides of formula II can be prepared in excellent practical conditions by reacting cyclam with POCl$_3$ in the presence of a base.

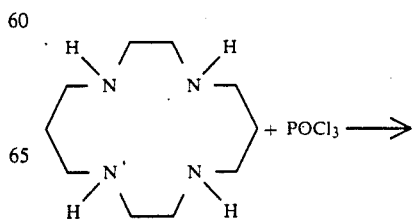

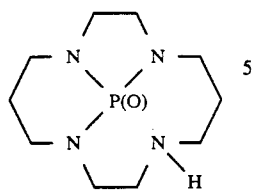

However, in accordance with the present invention, these intermediates are obtained in excellent yields according to the reaction scheme below, which constitutes a very marked improvement to the operating method described above.

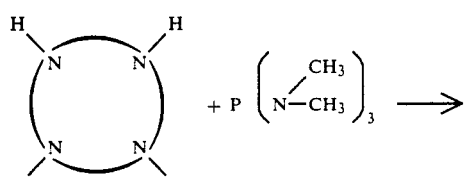

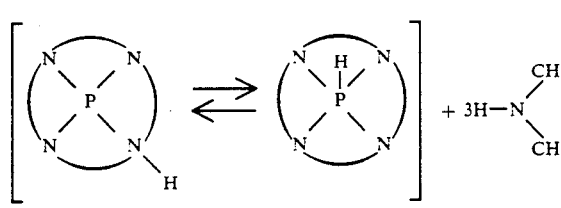

Intermediate 1

Intermediate 1 has been studied by J.E. Richman and T.J. Atkins (Tet. Lett. 1978, 52, 5149) and its characteristics are known; in particular it involves two forms in an equilibrium which is more or less displaced. This intermediate 1 is readily obtained merely by heating in an organic solvent (for example toluene); if the operation is carried out under a stream of dry nitrogen, the dimethylamine formed is entrained and the reaction is complete after a few hours. The progress of the reaction can be followed by the release of the amine formed into a stoichiometric quantity of acid containing a small quantity of colored indicator. At the turning point of the indicator the reaction is finished.

Intermediate 1 is treated with excess CCl$_4$. Intermediate 2 is then formed quantitatively:

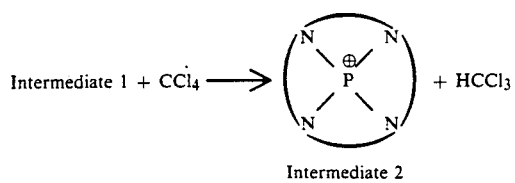

Hydrolysis of this intermediate 2 is carried out using dilute sodium hydroxide:

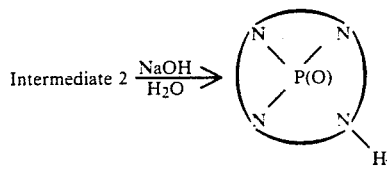

This set of operations is quantitative; the macroring triprotected with one P(0) is extracted with an organic solvent (dichloromethane) to be subsequently employed as in the monoalkylation stage.

The intermediate phosphorotriamide is alkylated very easily in the conventional conditions for the SN$_2$ reaction. The liberation of the tetramine from its protecting group takes place easily in acidic medium under reflux for a few hours. The monofunctionalization is thus preferably carried out in DMF, in the presence of a base, preferably sodium or potassium carbonate. As for the deprotection, this is carried out with 3M HCl.

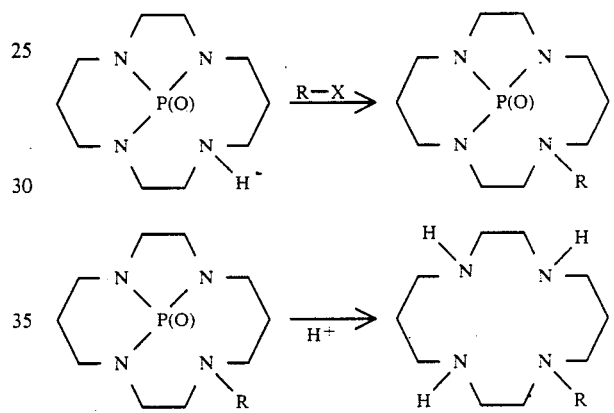

Furthermore, when an alcohol functional group is carried by a carbon bonded to another unsaturated carbon, this activated alcohol, for example benzl alcohol, can react directly with the intermediate 2.

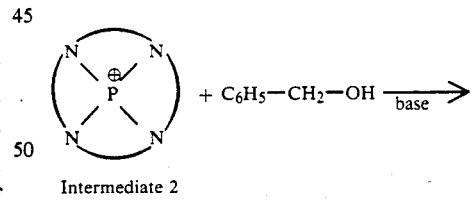

Intermediate 2

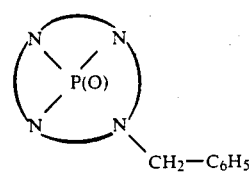

The yield from this stage is also quantitative and forms an advantageous alternative form of variant B.

VARIANT C

The third variant of the process according to the invention consists in preparing an intermediate of general formula II, triprotected with an intracyclic boron atom.

This triprotected intermediate can be obtained in various ways. It can be obtained, for example, by a transamination reaction with the aid of trisdimethylaminoborane.

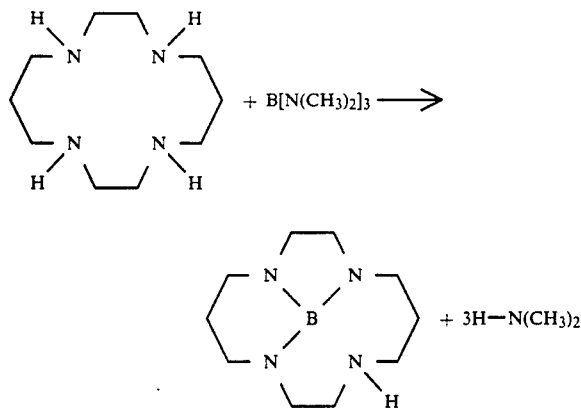

The reaction is conducted in an organic solvent, for example toluene; here too, the release of an amine may enable the reaction to be followed.

In the general operating method the solvent is evaporated off, the residue is taken up with a polar solvent for example, THF and an equivalent quantity of n-butyllithium is added. The anion thus formed is alkylated in excellent conditions.

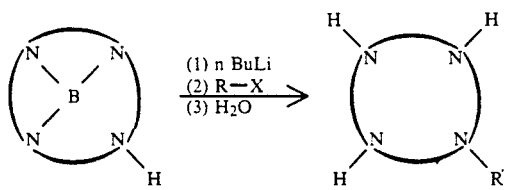

The chief advantage of this variant lies in the deprotection stage, which takes place very rapidly in very mild conditions: $H_2O$ is sufficient; nevertheless, a basic medium is adopted to make the extraction of the tetraazamacroring easier.

It will be noted that trisdimethylaminoborane can also be replaced with isopropyl or methyl orthoborate $B(OCH_3)_3$.

To summarize, each of these methods has its own field of application; nevertheless, we stress that in all cases stoichiometric methods are involved, no excess of ligand being necessary. The examples introduced below show that the triprotection is highly efficient; the nitrogen remaining free can generally be used in any of the usual alkylation reactions of secondary amines. Variant C is wholly original and allows the introduction of functional groups which would not withstand a prolonged acidic hydrolysis. Thus, the monomeric derivative cyclam—$CH_2$—$C_6H_4$—$CH=CH_2$ is prepared by this route alone, in superior yields. We also emphasize the rapidity of this latter method, which makes it possible to obtain a complete N-monoalkylation within a period of a few hours. In all cases, the products are of satisfactory quality and do not require any subsequent purification stage.

The process forming the subject of the present invention will be illustrated below with the aid of particular examples of use.

EXAMPLE 1

All these handling operations are performed with protection from air, under nitrogen.

Preparation of the chromium tricarbonyl complex of cyclam 1 g of cyclam (5 mmol) and 1.38 g of chromium hexacarbonyl (6 mmol) are placed in 50 ml of dry and deaerated dibutyl ether; the mixture is heated to the reflux temperature of the solvent for 2–3 hours. The cyclam $Cr(CO)_3$ complex precipitates. After cooling to room temperature, the solvent is removed by filtration under nitrogen and the solid is rinsed with diethyl ether and is then dried under vacuum at 40° C.; the excess $Cr(CO)_6$ is thus removed.

Alkylation and deprotection 0.278 g of cyclam $Cr(CO)_3$ (0.8 mmol), 96 µl of benzyl bromide (0.8 mmol) and an excess of sodium carbonate are placed in 5 ml of dry and deaerated DMF. The mixture is heated to 100° C. for 2 hours and is then cooled to room temperature; the solvent is evaporated off under vacuum and this residue is taken up in 20 ml of 6N HCl and is then oxidized with air. The mixture becomes green. The mixture is made basic to pH=14 by adding potassium hydroxide pellets and is then extracted with 2×25 ml of $CH_2Cl_2$; after drying of the organic phases the solvent is evaporated off; the oily residue is taken up in 5 ml of 10% strength sulfuric ethanol; the precipitate is filtered off, taken up in 5 ml of water, made basic and is then again extracted to give 0.176 g of pure N-benzylcyclam (62%).

Entirely identical results were obtained by replacing chromium hexacarbonyl with molybdenum hexacarbonyl.

EXAMPLE 2

Preparation of the complex 200 mg of cyclam (1 mmol) are placed in 40 ml of toluene and 1 mmol of tris(dimethylamino)phosphine is added. The mixture is heated to 100° C. This temperature is maintained until 3 mmol of dimethylamine are released. After cooling, 1 ml of dry $CCl_4$ is added slowly. The intermediate precipitates. Hydrolysis with 4M sodium hydroxide followed by extraction with dichloromethane allows the cyclam P(O) complex to be recovered quantitatively (Y>98%).

Alkylation and deprotection 300 mg of sodium carbonate are added to 30 ml of dry DMF containing the above compound. The mixture is heated to 100° C. and 130 µl (1 mmol) of benzyl bromide are added. After one hour's reaction the mixture is filtered, the solvent evaporated off, and the residue is then taken up with 15 ml of 4M hydrochloric acid. After cooling, the solution is made basic by adding sodium hydroxide and the aqueous solution is extracted several times with dichloromethane. The organic phases are dried and the solvent is stripped off by distillation. N-Benzylcyclam is thus obtained in a 95% yield.

EXAMPLE 3

The handling operations are performed with protection against air, under nitrogen, as far as the deprotection stage.

Preparation of the complex 200 mg of cyclam (1 mmol) are placed in 40 ml of toluene and 190 µl of tris(dimethylamino)borane are added. The mixture is heated to 100° C. This temperature is maintained until 3 mmol of dimethylamine have been released.

Alkylation and deprotection

The toluene is evaporated off using 30 ml of dry THF. After the complex has dissolved, the mixture is cooled to −30° C. and an equivalent quantity of n-butyllithium is added. The mixture is kept stirred at −30° C. for 15 min. After the addition of 130 µl of benzyl bromide (1 mmol), it is allowed to return to room temperature; stirring is continued for approximately 2 hours.

The complex is destroyed by adding a few drops of water.

The THF is removed by vacuum distillation. The residue is treated with 30% strength sodium hydroxide and is then extracted twice with 25 ml of $CH_2Cl_2$. After drying of the organic phases, the solvent is evaporated off. The monoalkylation compound is in the form of a yellow oil. Yield=95%.

Each of the variants described in detail in the context of the abovementioned Examples 1 to 3 has been successfully employed in a satisfactory manner to obtain the following compounds. The halide employed may be chosen from the chloride, a bromide, and iodide or else an alkyl, aryl or aralkyl tosylate.

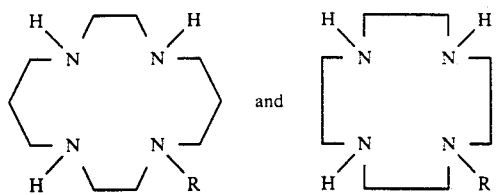

in which:
R = —$CH_2$—$\phi$
R = —$CH_2$—CH=$CH_2$
R = n—$C_{12}H_{25}$
R = —$CH_3$
R = —$(CH_2)_3$—$\phi$
R = $CH_2$—ferrocene
R = $CH_2$—$C_6H_4$—CH=$CH_2$ (meta+para isomer)

The compound below was obtained by bringing the complex and the corresponding organic dihalide into contact in proportions of 2:1.

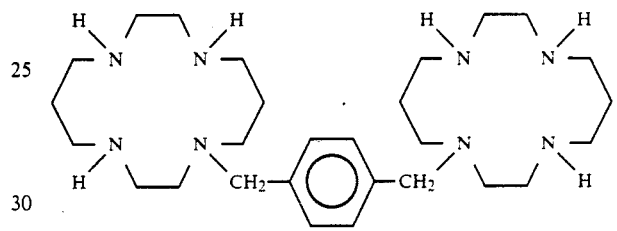

The results obtained are collected in Table I, introduced below.

TABLE I

| COMPOUND | YIELD | VARIANT | ALKYLATING AGENT |
|---|---|---|---|
| Derivatives of (2222) | 95% | A: $Cr(CO)_3L$ | $C_6H_5CH_2Br$ |
|  | 75% | A: $Mo(CO)_3L$ | " |
|  | 70% | A: $W(CO)_3L$ | " |
|  | 90% | B | " |
|  | 50% | C | " |
| Derivatives of 2323 |  |  |  |
| R = $CH_2$—$C_6H_5$ | 97% | A: $Cr(CO)_3L$ | $C_6H_5CH_2Br$ |
|  | 87% | A: $Mo(CO)_3L$ | " |
|  | 85% | A: $W(CO)_3L$ | " |
|  | 80% | B | $C_6H_5CH_2OH$ |
|  | 95% | B | $C_6H_5CH_2Br$ |
|  | 95% | C | " |
| R = $CH_3$ | 30% | A: $Cr(CO)_3L$ | $CH_3I$ |
|  | 30% | B | $CH_3I$ |
|  | 80% | C | $CH_3$—O—Ts |
| R = —$(CH_2)_3$—$C_6H_5$ | 75% | B | R—Br |
|  | 90% | C | R—OTs |
| R = $C_{12}H_{25}$ | 30% | A: $Cr(CO)_3L$ | R—Br |
|  | 70% | B | R—Br |
| R = —$CH_2$—CH=$CH_2$ | 55% | A: $Cr(CO)_3L$ | R—Br |
|  | 70% | B | R—OH |
|  | 80% | B | R—OH |

TABLE I-continued

| COMPOUND | YIELD | VARIANT | ALKYLATING AGENT |
|---|---|---|---|
| R = —CH$_2$-ferrocene | 80% | C | R—Br |
|  | 80% | A: Cr(CO)$_3$L | R—Cl |
|  | 80% | B | R—OH |
|  | 80% | B | R—Cl |
|  | 80% | C | R—Cl |
| R = —CH$_2$—C$_6$H$_4$—CH=CH$_2$ commercial mixture of meta + para isomers | 95% | C | R—Cl |
| Bicylic derivatives | | | |
| Isomer ortho | 45% | B | BrCH$_2$—C$_6$H$_4$—CH$_2$Br |
| meta | 80% | B | " |
| para | 90% | A: Cr(CO)$_3$L | " |
| para | 90% | B | " |
| Derivative of 3333 | 90% | B | C$_6$H$_5$CH$_2$Br |
|  | 80% | C | " |
| Derivative of 3434 | 90% | B | C$_6$H$_5$CH$_2$Br |
|  | 70% | C | " |

We claim:

1. Process for the preparation of monofunctionalized cyclic tetramines of formula I

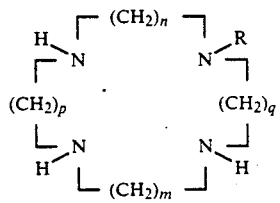

in which:
- $m=n=p=q=2$, or
- $m=n=2$; $p=q=3$, or
- $m=2$; $n=p=q=3$, or
- $n=2$; $m=p=q=3$, or
- $m=n=p=q=3$, or
- $m=n=3$; $p=q=4$, and R denotes a saturated or unsaturated, especially polymerizable, substituted or unsubstituted alkyl radical, comprising the steps of:
preparing a triprotected tetraazacycloalkane compound, of formula II

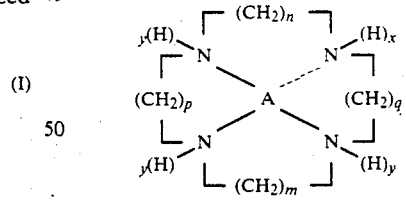

in which
x and y denote, independently of each other, 1 or 0,
at least three of the four nitrogen atoms are bonded, via covalent bonds, with A, where A is selected from the group consisting of a Boron atom, P(O) group, P(+) group and a metal carbonyl group M(CO), with M being Cr, Mo or W, and
the broken line denotes a covalent bond which may be formed between the fourth nitrogen atom and A; in that the triprotected tetraazacycloalkane compound of formula III $$R—X \qquad (III)$$

in which:

R has the meaning given in connection with formula I, and X denotes a halogen or a tosylate radical, to obtain a triprotected and monofunctionalized tetraazacycloalkane compound of formula IV

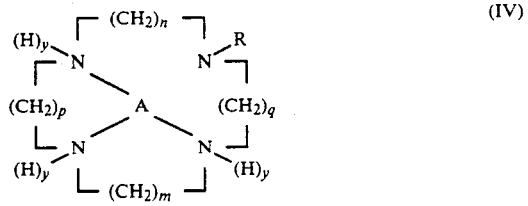

and in that A is removed from the compound of formula IV to obtain the corresponding compound of formula I.

2. Process according to claim 1, characterized in that in formulae II an IV the symbol A denotes a boron atom, a metal carbonyl group M(CO)$_3$ where M is chosen from Cr, Mo and W, or a P(O) or P(+) group.

3. Process according to claim 1 characterized in that a compound of formula II is prepared, in which A denotes CR(CO)$_3$ and, after monofunctionalization, the chromium tricarbonyl complex is deprotected by air oxidation and at acidic pH.

4. Process according to claim 3, characterized in that the compound of formula II, in which A denotes Cr(CO)$_3$, is obtained by reaction of the corresponding tetraazacycloalkane compound of formula I with chromium hexacarbonyl.

5. Process according to claim 1 characterized in that a compound of formula II is prepared, in which A denotes P(O) and, after monofunctionalization, the phosphorotriamide compound is deprotected in acidic medium.

6. Process according to claim 5, characterized in that the compound of formula II, in which A denotes P(O), is obtained by reaction of the corresponding tetraazacycloalkane compound of formula I with P(N(CH$_3$)$_2$)$_3$, treatment of the said formed intermediate with CCl$_4$ and then basic hydrolysis.

7. Process according to claim 1 characterized in that a compound of formula II is prepared, in which A denotes a P(+) group bonded via a covalent bond to each of the 4 nitrogen atoms and, after monofunctionalization, the phosphorotriamide compound is deprotected in acidic medium.

8. Process according to claim 7, characterized in that the compound of formula II in which A denotes P(+) bonded via a covalent bond to each of the four nitrogen atoms is obtained by reaction of the corresponding tetraazacycloalkane compound of formula I with P(N(CH$_3$)$_2$)$_3$, and then treatment with CCl$_4$ of the said intermediate obtained.

9. Process according to claim 1 characterized in that a compound of formula II is prepared, in which A denotes a boron atom and, after monofunctionalization, the borotriamine compound is deprotected by simple hydrolysis.

10. Process according to claim 9, characterized in that the compound of formula II in which A denotes a boron atom is obtained by reaction of the corresponding tetraazacycloalkane compound of formula I with tris-dimethylaminoborane B[N(CH$_3$)$_2$]$_3$ or of methyl orthoborate B(OCH$_3$)$_3$.

11. Process according to claim 1 characterized in that the organic compound of formula III is an organic dihalide leading to the formation of a bimacrocyclic compound of formula I.

12. Process according to claim 11, characterized in that the organic compound of formula III is 1,4-di(-chloromethyl)benzene.

* * * * *